(12) United States Patent
Morimoto et al.

(10) Patent No.: US 9,278,032 B2
(45) Date of Patent: Mar. 8, 2016

(54) SMALL-SIZED DISPOSABLE PULL-ON DIAPER

(75) Inventors: Koichi Morimoto, Beijing (CN); Takashi Umeo, Nishinomiya (JP); Hiroyuki Ueno, Kobe (JP); Katsuhiro Yonemura, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 5 days.

(21) Appl. No.: 13/494,069

(22) Filed: Jun. 12, 2012

(65) Prior Publication Data

US 2013/0138072 A1 May 30, 2013

Related U.S. Application Data

(60) Provisional application No. 61/564,873, filed on Nov. 30, 2011.

(51) Int. Cl.
*A61F 13/15* (2006.01)
*A61F 13/49* (2006.01)

(52) U.S. Cl.
CPC ..... *A61F 13/15593* (2013.01); *A61F 13/49001* (2013.01); *A61F 13/49011* (2013.01); *A61F 13/49017* (2013.01); *A61F 13/4902* (2013.01)

(58) Field of Classification Search
CPC ............... A61F 13/64; A61F 13/4902; A61F 13/49025; A61F 13/49011; A61F 13/15593
USPC ............ 604/385.24, 385.25, 385.26, 385.27, 604/385.29, 385.3
See application file for complete search history.

(56) References Cited

U.S. PATENT DOCUMENTS

| | | | |
|---|---|---|---|
| 2,733,715 A * | 2/1956 | Folk | 604/398 |
| 3,560,292 A | 2/1971 | Butter | |
| 3,898,117 A | 8/1975 | Taylor | |
| 4,333,978 A | 6/1982 | Kocher | |
| 4,450,026 A | 5/1984 | Pieniak et al. | |
| 4,515,595 A | 5/1985 | Kievit et al. | |
| 4,606,964 A | 8/1986 | Wideman | |
| 4,642,150 A | 2/1987 | Stemmler | |
| 4,642,819 A | 2/1987 | Ales et al. | |
| 4,675,068 A | 6/1987 | Lundmark | |
| 4,710,189 A | 12/1987 | Lash | |
| 4,854,985 A | 8/1989 | Soderlund et al. | |
| 4,854,989 A | 8/1989 | Singheimer | |
| 4,995,928 A | 2/1991 | Sabee | |
| 5,091,039 A | 2/1992 | Ujimoto et al. | |

(Continued)

FOREIGN PATENT DOCUMENTS

| | | |
|---|---|---|
| CN | 101909568 | 12/2010 |
| JP | H10060745 | 3/1998 |

(Continued)

OTHER PUBLICATIONS

PCT International Search Report, PCT/US2012/038940 date of mailing Jul. 20, 2012.

(Continued)

*Primary Examiner* — Jacqueline Stephens
(74) *Attorney, Agent, or Firm* — Richard L. Alexander; Ikuko Fujie

(57) ABSTRACT

A small-sized disposable pull-on diapers having optimized waist circumferential length and leg opening length. The small-sized disposable pull-on diapers have a better performance in ease of application and waist and leg fit.

20 Claims, 8 Drawing Sheets

(56) References Cited

U.S. PATENT DOCUMENTS

| | | | |
|---|---|---|---|
| 5,209,801 A | 5/1993 | Smith | |
| 5,221,390 A | 6/1993 | Persson et al. | |
| 5,232,777 A | 8/1993 | Sipinen et al. | |
| 5,236,539 A | 8/1993 | Rogberg et al. | |
| 5,447,508 A | 9/1995 | Numano et al. | |
| 5,624,420 A | 4/1997 | Bridges et al. | |
| 5,660,657 A | 8/1997 | Rajala et al. | |
| 5,735,839 A | 4/1998 | Kawaguchi et al. | |
| 5,749,865 A | 5/1998 | Yamamoto et al. | |
| 5,766,389 A | 6/1998 | Brandon et al. | |
| 5,941,865 A | 8/1999 | Otsubo et al. | |
| 6,033,502 A | 3/2000 | Coenen et al. | |
| 6,443,935 B1 | 9/2002 | Gustafsson et al. | |
| 6,569,275 B1 | 5/2003 | Popp et al. | |
| 6,595,976 B2 | 7/2003 | Jitoe et al. | |
| 6,685,690 B2 | 2/2004 | Ikeda et al. | |
| 6,808,582 B2 | 10/2004 | Popp et al. | |
| 6,811,638 B2 | 11/2004 | Close et al. | |
| 6,833,179 B2 | 12/2004 | May et al. | |
| 6,913,664 B2 | 7/2005 | Umebayashi et al. | |
| 6,981,968 B2 | 1/2006 | Kusibojoska et al. | |
| 7,029,545 B2 | 4/2006 | Suzuki | |
| 7,291,138 B2 | 11/2007 | Hoshino et al. | |
| 7,316,840 B2 | 1/2008 | Neculescu et al. | |
| 7,331,946 B2 | 2/2008 | Shimada et al. | |
| 7,335,273 B2 | 2/2008 | Neculescu et al. | |
| 7,632,259 B2 | 12/2009 | Elfström et al. | |
| 7,727,214 B2 | 6/2010 | Torigoshi et al. | |
| 7,727,217 B2 | 6/2010 | Hancock-Cooke | |
| 7,862,549 B2 | 1/2011 | Desai et al. | |
| 7,901,393 B2 | 3/2011 | Matsuda et al. | |
| 8,053,074 B2 | 11/2011 | Miyamura et al. | |
| 8,105,303 B2 | 1/2012 | Sakaguchi | |
| 8,114,058 B2 | 2/2012 | Otsubo et al. | |
| 8,128,609 B2 | 3/2012 | Erdman et al. | |
| 8,142,590 B2 | 3/2012 | Rajala et al. | |
| 8,221,376 B2 | 7/2012 | Otsubo et al. | |
| 8,282,617 B2 | 10/2012 | Kaneda | |
| 8,308,706 B2 | 11/2012 | Fukae | |
| 8,348,915 B2 | 1/2013 | Vasic et al. | |
| 8,348,919 B2 | 1/2013 | Langdon et al. | |
| 8,357,133 B2 | 1/2013 | Vasic et al. | |
| 8,440,043 B1 | 5/2013 | Schneider et al. | |
| 8,518,009 B2 | 8/2013 | Saito et al. | |
| 8,518,010 B2 | 8/2013 | Kuwano et al. | |
| 8,647,319 B2 | 2/2014 | Een et al. | |
| 8,672,912 B2 | 3/2014 | Corneliusson et al. | |
| 8,672,915 B2 | 3/2014 | Kuwano et al. | |
| 8,690,850 B2 | 4/2014 | Hardegree | |
| 2002/0188268 A1 | 12/2002 | Kline et al. | |
| 2003/0181883 A1 | 9/2003 | Olson et al. | |
| 2004/0006323 A1 | 1/2004 | Hall et al. | |
| 2005/0106971 A1 | 5/2005 | Thomas | |
| 2006/0157188 A1 | 7/2006 | Thorson et al. | |
| 2007/0141311 A1 | 6/2007 | Mleziva et al. | |
| 2007/0208317 A1 | 9/2007 | Krautkramer et al. | |
| 2007/0289697 A1 | 12/2007 | Een et al. | |
| 2009/0030392 A1* | 1/2009 | Kanai et al. | 604/385.01 |
| 2010/0076394 A1 | 3/2010 | Hayase et al. | |
| 2010/0221496 A1 | 9/2010 | de Jong | |
| 2010/0252178 A1 | 10/2010 | Takino et al. | |
| 2010/0318054 A1 | 12/2010 | Langdon et al. | |
| 2011/0112499 A1 | 5/2011 | Trennepohl et al. | |
| 2011/0178489 A1 | 7/2011 | Baba et al. | |
| 2011/0319853 A1 | 12/2011 | Yamashita et al. | |
| 2012/0086145 A1 | 4/2012 | Nakamura et al. | |
| 2012/0226254 A1 | 9/2012 | Takino | |
| 2012/0289921 A1 | 11/2012 | Hashino et al. | |
| 2013/0006207 A1 | 1/2013 | Roe et al. | |
| 2013/0102982 A1 | 4/2013 | Nakano et al. | |
| 2013/0102987 A1 | 4/2013 | Mukai et al. | |
| 2013/0138072 A1 | 5/2013 | Morimoto et al. | |
| 2013/0149925 A1 | 6/2013 | Handziak et al. | |
| 2013/0211363 A1 | 8/2013 | LaVon et al. | |
| 2013/0310792 A1 | 11/2013 | Desai et al. | |
| 2013/0324957 A1 | 12/2013 | Gassner et al. | |
| 2013/0338623 A1 | 12/2013 | Kinoshita et al. | |

FOREIGN PATENT DOCUMENTS

| | | |
|---|---|---|
| JP | H10225481 | 8/1998 |
| JP | 10314225 | 12/1998 |
| JP | 2000093461 | 4/2000 |
| JP | 2000160460 | 6/2000 |
| JP | 2002275738 | 9/2000 |
| JP | 2003020551 | 1/2003 |
| JP | 2005060892 | 3/2005 |
| JP | 2006214054 | 8/2006 |
| JP | 2007023417 | 2/2007 |
| JP | 2008-131968 | 6/2008 |
| JP | 2009261981 | 11/2009 |
| JP | 2012026044 | 2/2012 |
| JP | 2012100832 | 5/2012 |
| JP | 2012120571 | 6/2012 |
| JP | 2013255841 | 12/2013 |

OTHER PUBLICATIONS

Written Opinion, PCT/US2012/038940 date of mailing Jul. 20, 2012.

* cited by examiner

SMALL-SIZED DISPOSABLE PULL-ON DIAPER

CROSS REFERENCE TO RELATED APPLICATION

This application claims the benefit of U.S. Provisional Patent Application No. 61/564,873, filed on Nov. 30, 2011, the substance of which is incorporated herein by reference.

FIELD OF THE INVENTION

The present disclosure relates to disposable pull-on diapers which can be donned by inserting the wearer's legs into the leg openings and sliding the diaper up into position about the lower torso. Particularly, the present disclosure relates to small-sized disposable pull-on diapers.

BACKGROUND OF THE INVENTION

Disposable pull-on diapers have been well known and successfully commercialized. For example, WO 2006/017718 describes a disposable pull-on diaper having a waist opening and two leg openings. The disposable pull-on diaper comprises an absorbent main body and a ring-like elastic belt. The absorbent main body comprises a liquid pervious topsheet, a liquid impervious backsheet, and an absorbent core disposed therebetween. The ring-like elastic belt comprises a belt substrate layer and a belt elastic material joined to the belt substrate layer. The two longitudinal ends of the absorbent body are joined to the ring-like elastic belt in front and back.

Tape-type and pull-on type diapers are the two main types of disposable diapers. Pull-on diapers are recently increasing popularity due to the convenience of applying a pull-on diapers on an infant. When putting a tape-type diaper on an infant, to achieve comfortable fit, a care-taker needs to pay close attention to the positioning of the diaper relative to the infant's body and the stretching level applied in taping diaper's ears to its landing zone. In contrast, pull-on diapers have predefined waist opening and leg openings and thus allows a care-taker to put the diapers on an infant's body by simply inserting the infant's legs in the leg opening and pulling the diaper up over the waist. So far, pull-on diapers have mainly been successful in large and medium sized diapers. However, there is much area for improvement for pull-on diapers in small size.

Small-sized diapers are intended for use on infants having body weight of less than 8 kilograms. Infants of this body size are typically less than 10 months old and in average, they sleep about 13-18 hours a day. For them, diapers are more likely changed while they are sleeping. Hence, it is desirable that the small-sized diapers can be applied onto the infants with ease so that their sleep will not be disturbed. Furthermore, small-sized infants typically have thighs of greater circumference but smaller waist than medium and large sized infants. In addition, the legs of small-sized infants are usually not in a straightened state, but are more often in a curved position which requires a wider waist opening to put the diaper through the curved legs. Hence, to simply downsize medium and large sized pull-on diapers to small size would not provide desirable waist and leg fit as well as the desirable ease of application.

Also, it has been found that currently commercialized small-sized pull-on diapers are not stretchable enough to be applied with ease. Some have also been found not to fit well in legs. Therefore, there is still a need for a small-sized disposable pull-on diaper which can be applied with ease and can fit the waist and legs of a wearer better.

SUMMARY OF THE INVENTION

The present disclosure addresses the aforementioned need by providing a small-sized disposable pull-on diaper having optimized dimensions. Particularly, the small-sized disposable pull-on diaper of the present disclosure discloses an absorbent main body and a ring-like elastic belt.

The absorbent main body comprises a liquid pervious topsheet, a liquid impervious backsheet, and an absorbent core disposed therebetween. The absorbent main body has left and right longitudinally extending side edges, front and back transversely extending end edges, longitudinally opposing front and back waist panels, and a crotch panel between the waist panels. At least one leg elastic material is disposed in proximity to each of said side edges and extends generally longitudinally along said side edges.

The ring-like elastic belt comprises a front and a back belt portion joined to each other at side seams. Each of the front and back belt portion has transversely extending proximal and distal edges. The distal edge of the ring-like elastic belt defines a waist opening. The proximal edge is located closer than the distal edge relative to the crotch panel of the absorbent main body. Each of the front belt portion and back belt portion of the ring-like belt has a central panel, and left and right side panels contiguous with its central panel. The ring-like elastic belt comprises a belt substrate layer and a plurality of waist elastic strands and a plurality of side panel elastic strands each extending in the transverse direction and attached to the belt substrate layer. The waist elastic strands are disposed in proximity to the distal edge of the front and back belt portions and the side panel elastic strands are disposed at least in the left and right side panels. The ring-like elastic belt has a stretched waist circumferential length and a free-state waist circumferential length.

The central panel of the front belt portion of the ring-like belt is joined to the front waist panel of the absorbent main body, the central panel of the back belt portion of the ring-like belt is joined to the back waist panel of the absorbent main body, and the proximal edge of the respective left and right side panels of the front belt portion and the back belt portion together with the left and right side edges of the crotch panel of the absorbent main body defines two leg openings, each of the leg opening has a leg opening length.

The stretched waist circumferential length is from about 620 mm to 700 mm, optionally from about 640 mm to 680 mm, and the ratio of the stretched waist circumferential length to the free-state waist circumferential length is from about 2.5 to about 2.8. The leg opening length is from about 250 mm to about 300 mm, optionally from about 265 mm to 285 mm. In a preferred embodiment, the leg opening length of the diaper includes a leg elastic length which is from about 50% to 75%, optionally from about 68% to about 72% of the leg opening length.

Inventors of the present disclosure have surprisingly found that the small-sized disposable pull-on diapers of the present disclosure having the aforementioned optimized dimensions deliver the benefits of both ease of application and better waist and leg fit.

BRIEF DESCRIPTION OF THE DRAWINGS

While the specification concludes with claims particularly pointing out and distinctly claiming the subject matter which is regarded as forming the present disclosure, it is believed that the invention will be better understood from the following description which is taken in conjunction with the accompanying drawings and which like designations are used to designate substantially identical elements, and in which:

DETAILED DESCRIPTION OF THE INVENTION

As used herein, the term "pull-on diaper" refers to diapers which have a defined waist opening and a pair of leg openings and which can be pulled onto the body of wearers by inserting their legs into the leg openings and pulling the article up over their waists. The term "small sized diaper", also known as "S size" diaper refers to diapers for infants having a body weight of less than 8 kilograms. Medium sized diaper", also known as "M size" diapers refers to diapers for infants having a body weight of from about 7 kilograms to about 10 kilograms. "Large sized diaper", also known as "L size" diapers refers to diapers for infants having a body weight of from about 9 kilograms to about 14 kilograms.

Figure 1:
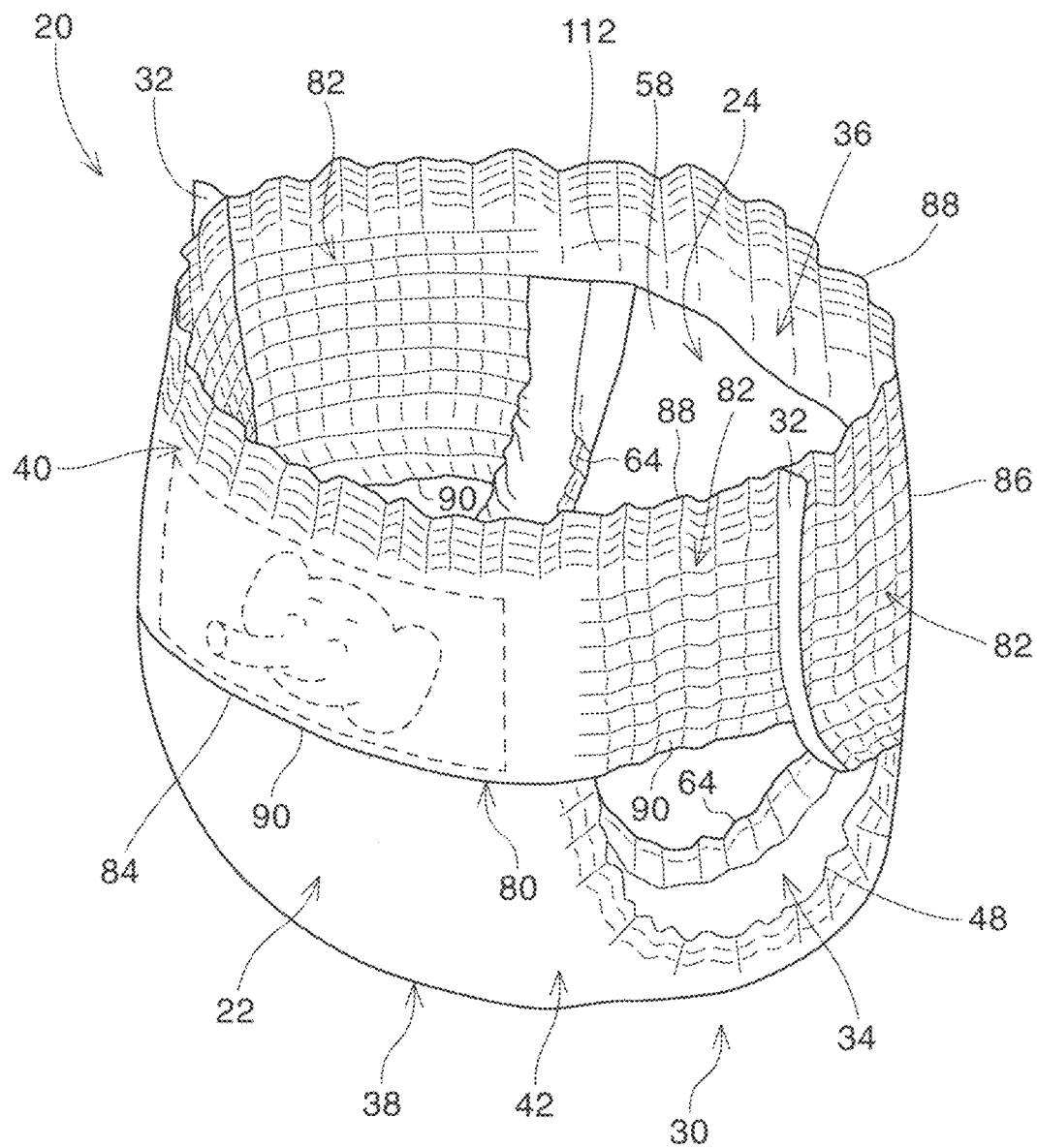
FIG. 1 is a perspective view of a preferred embodiment of the disposable pull-on diaper of the present disclosure in an in-use configuration.
Figure 2:
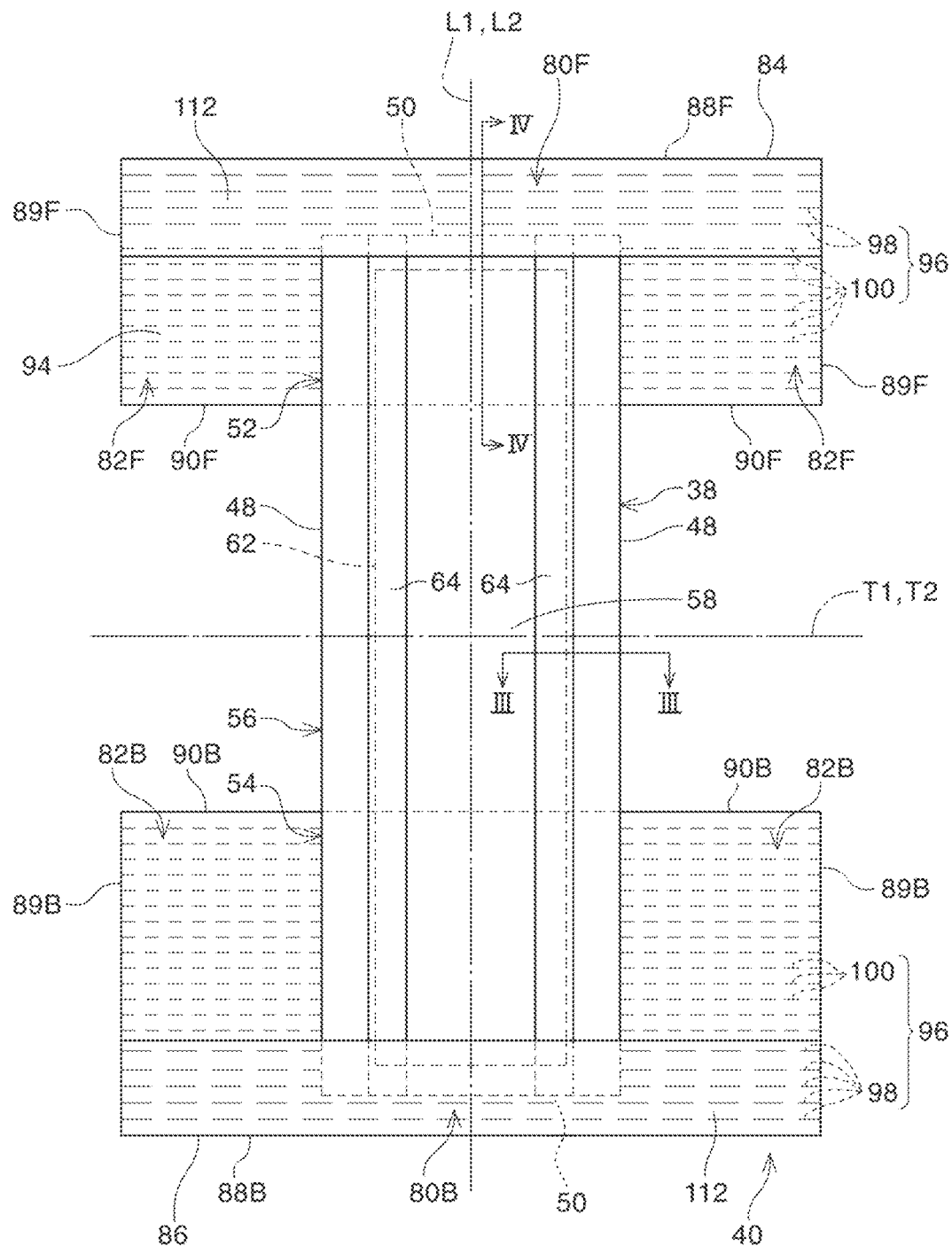
FIG. 2 is a top plan view of a preferred embodiment of the pull-on diaper in its flat free-state condition with the front belt portion and back belt portion separated and showing the inner surface of the diaper.

A preferred embodiment of the small sized disposable pull-on diaper 20 of the present disclosure is shown in FIG. 1. FIG. 1 is a perspective view of the pull-on diaper 20 of the present disclosure in an in-use configuration. FIG. 2 is a top plan view of the pull-on diaper shown in FIG. 1 in its flat free-state configuration with the front belt portion and back belt portion separated and with the inner surface of the diaper shown. The pull-on diaper 20 has an outer surface 22, an inner surface 24 opposed to the outer surface 22. The pull-on diaper 20 has a longitudinal centerline L1 and a transverse centerline T1. The diaper 20 comprises an absorbent main body 38 (hereinafter may be simply referred to as "main body") to cover the crotch region of the wearer, and a ring-like elastic belt 40 (hereinafter may be simply referred to as "elastic belt").

The Absorbent Main Body

The absorbent main body 38 absorbs and contains body exudates in use. In the embodiment shown in FIGS. 1 and 2, the main body 38 has a generally rectangular shape having a longitudinal centerline L2, a transverse centerline T2, left and right longitudinally extending side edges 48 (hereinafter may be referred to as "longitudinal side edge" or "side edge") and front and back transversely extending end edges 50 (hereinafter may be referred to as "transverse end edge" or "end edge"). The main body 38 has a front waist panel 52, a back waist panel 54 and a crotch panel 56 between the front and back waist panels 52, 54. As used herein, "front" refers to the direction that a wearer is facing when the diaper is worn and "back" refers to the direction of a wearer's back when the diaper is worn. The main body may have shapes other than rectangle, such as an hour-glass shape with the crotch panel 56 has an inwardly curved side edges.

Figure 3:
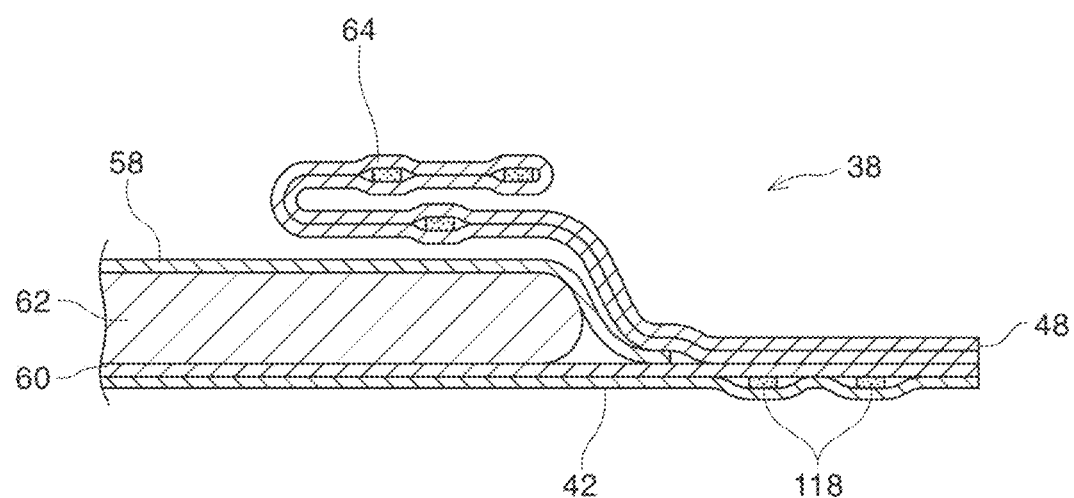
FIG. 3 is a cross-sectional view of FIG. 2 taken along the line III-III.

Referring to FIG. 3, the main body 38 comprises a liquid pervious topsheet 58, a liquid impervious backsheet 60 and an absorbent core 62 disposed there between. At least one leg elastic material 118 is disposed in proximity to each of the longitudinal side edges 48 and extends generally along the longitudinal side edges. The main body 38 may additionally comprise a barrier leg cuff 64 disposed along the longitudinal side edges 48. The barrier leg cuff 64 provides improved containment of liquids and other body exudates in the main body. The materials for making barrier leg cuff and the structure of barrier leg cuff are well known in the art, for example, as described in WO 2006/017718.

The liquid pervious topsheet 58 is optionally positioned adjacent to the body-facing surface of the absorbent core 62 and may be joined thereto and/or to the backsheet 60 by any attachment means known in the art. The liquid impervious backsheet 60 is generally that portion of the diaper 20 positioned adjacent to the garment-facing surface of the absorbent core 62 and prevents exudates absorbed and contained therein from soiling articles that may contact the diaper 20. The absorbent core is positioned between the topsheet 58 and the backsheet 60 and absorbs and retains body exudates. The topsheet 58, the backsheet 60 and the absorbent core may be manufactured from any known materials. Suitable topsheet materials may include porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the diaper while still preventing exudates from passing through the backsheet. Suitable absorbent core materials may include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

An outer cover layer 42 can be disposed on the outer surface 22 of the diaper 20 and covers at least the crotch panel 56 of the absorbent main body 38. The outer cover layer 42 may extend into and cover the front and back waist panels 52, 54 of the main body 38. The outer cover layer 42 is directly joined to and covers the liquid impervious backsheet 60 of the main body 38. Referring back to FIG. 2, the central panel 80 of the front and back belt portions 84, 86 (explained herein below) is joined to the front and back waist panels 52, 54 of the main body 38 through the outer cover layer 42. Thus, the outer cover layer 42 is sandwiched between the front and back belt portions 84, 86 and the liquid impervious backsheet 60 of the main body 38. The outer cover layer 42 may comprise any known materials and may comprise materials as used for the front and back belt portions 84, 86 as explained above. Optionally the outer cover layer 42 comprises a single layer of nonwoven web of synthetic fibers. More optionally, the outer cover layer 42 comprises a single layer of hydrophobic, non-stretchable nonwoven material.

The topsheet, absorbent core, backsheet and outer cover may be laterally and/or longitudinally coextensive. However, in a preferred embodiment, the absorbent core has a narrower lateral width than that of the topsheet and backsheet, and the topsheet has a narrower lateral width than that of the backsheet. In the embodiment shown in FIGS. 2 and 3, the outer cover layer 42 is coextensive with the liquid impervious backsheet 60 which have a bigger lateral width than the topsheet 58 and absorbent core 62. Where the topsheet, backsheet, absorbent core and outer cover have different lateral width or longitudinal length, the longitudinal side edges 48 and transverse end edges 50 of the absorbent body refer to the edges of the member which laterally and/or longitudinally extends the most.

At least one leg elastic material 118 is disposed in proximity to the side edges 48 and generally extends longitudinally along the side edges of the absorbent body 38. The leg elastic material can be in the form of elastic strand or ribbon attached to the backsheet in an extended state. As used herein, the terms "strand" and "ribbon" refer to material in long and thin configuration and these two terms can be used interchangeably. In the embodiment shown in FIG. 3, the leg elastic material 118 is disposed between the outer cover layer 42 and backsheet 60. The leg elastic material 118 may be disposed at least in the crotch panel 56 of the absorbent body 38 or may be disposed along the entirety of the longitudinal side edge 48.

Ring-Like Elastic Belt

Referring to FIGS. 1 and 2, the ring-like elastic belt 40 comprises a front belt portion 84 and a back belt portion 86 (hereinafter may be referred to as "front and back belt portions 84, 86). Each of the front belt portion 84 and the back belt portion 86 has central panels 80F, 80B and side panels 82F, 82B contiguous with the central panels 80F, 80B and positioned transversely outward from the central panels 80F, 80B. Herein, a front member and a back member may be indicated by a reference number with "F" suffix and "B" suffix, respectively, as necessary. Therefore, the "central panels 80F, 80B" for example indicates the "front central panel 80F" and the "back central panel 80B". The "central panel 80" also may mean the "front central panel 80F" and the "back central panel 80B". Each of the front and back belt portions 84, 86 has a transversely extending distal edge 88F, 88B, a transversely extending proximal edge 90F, 90B, and a longitudinally extending left and right side edge 89F, 89B, respectively. Herein, the term "proximal" is used to indicate the position that is relatively closer to the crotch panel of the main body. Therefore, the proximal edge 90F, 90B is located closer than the distal edge 88F, 88B relative to the crotch panel 56 of the main body 38. The central panels may partly or entirely overlap with the front and back waist panels 52, 54 of the main body 38 respectively. However, the central panels 80F, 80B does not extend into the crotch panel 56 of the main body 38 and is not disposed in the crotch panel 56. In the embodiment shown in FIG. 2, the central panels 80F, 80B partly overlaps with and is joined to the front and back waist panels 52, 54 of absorbent body, respectively. The front and back belt portions 84, 86 are joined at or adjacent to the side edges 89F, 89B by side seams 32 to form the ring-like elastic belt. The distal edges 88F and 88B define a waist opening 36. The proximal edges 90F, 90B of side panels 82F 82B together with the longitudinal side edges of the crotch panel 56 of absorbent body 38 define two leg openings 34.

Figure 4:
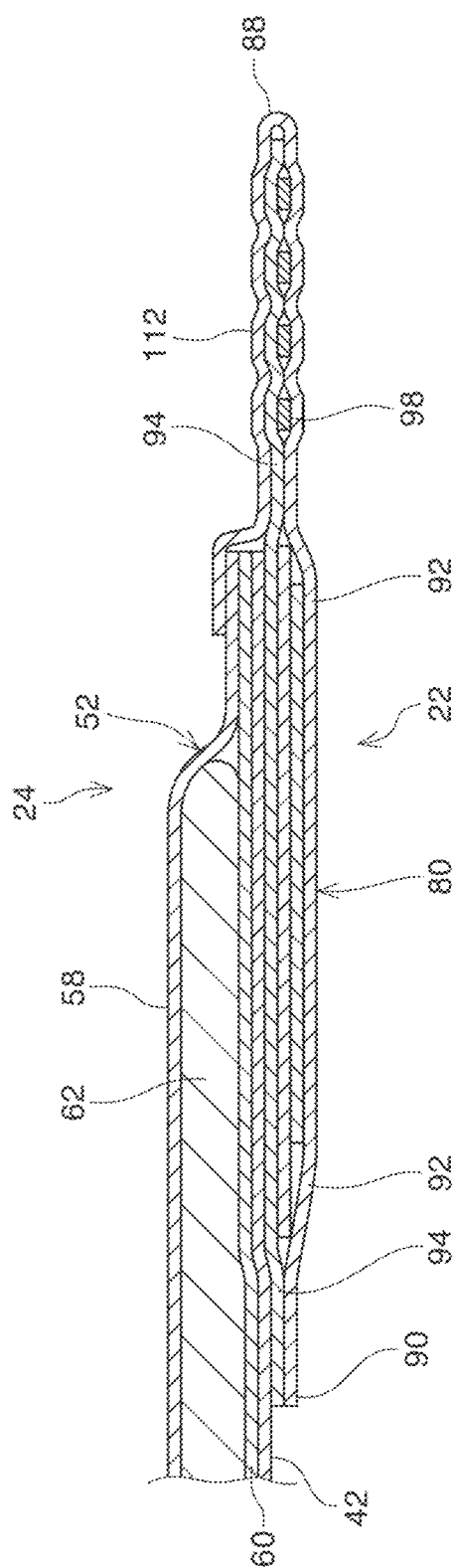
FIG. 4 is a cross-sectional view of FIG. 2 taken along the line IV-IV.

The ring-like elastic belt 40 comprises a belt substrate layer 92 (shown in FIGS. 4 and 7) and a plurality of waist elastic strands 98 and a plurality of side panel elastic strands 100 (hereinafter may be collectively referred to as belt elastic strands 96). Optionally, the ring-like elastic belt further comprises an inner layer 94 so that the belt elastic strands 96 are interposed between the two layers 92 and 94. The front and back belt portions 84, 86 may comprise the same material and/or may have the same structure. Alternatively, the front and back belt portions 84, 86 may comprise different materials and/or may have different structures. In the embodiment of FIG. 2, the front and back belt portions 84, 86 generally have the same layer structure. The belt substrate layer 92 and inner layer 94 can be manufactured from a wide range of materials such as plastic films; apertured plastic films; woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. Optionally, the belt substrate layer 92 and inner layer 94 comprise a nonwoven web of synthetic fibers. More optionally, the belt substrate layer 92 and inner layer 94 comprise hydrophobic, non-stretchable nonwoven material.

The plurality of waist elastic strands 98 are attached to the belt substrate layer 92 in proximity to the distal edge 88 and the side panel elastic strands 100 are attached to the belt substrate layer at least in both left and right side panels 82. The waist elastic strands 98 and side panel elastic strands 100 comprise one or more of elastic strands extending in the transverse direction. The plurality of waist elastic strands 98 and the plurality of side panel elastic strands 100 are attached to the belt substrate layer 92 or interposed between the belt substrate layer 92 and the inner layer 94 by adhesives under stretched condition such that the front and back belt portions 84, 86 provides elasticity when the diaper 20 is used.

In the embodiment shown in FIG. 2, waist elastic strands 98 and side panel elastic strands 100 are disposed at a constant interval in the longitudinal direction. Alternatively, the waist elastic strands 98 and the side panel elastic strands 100 may be disposed at a different interval in the longitudinal direction. The different longitudinal intervals can provide an improved fit to a wearer's body anatomy. For example, waist elastic strands can be disposed at a smaller longitudinal interval than that of side panel elastic strands. The waist elastic strands 98 can run continuously from the left longitudinal side edge to the right longitudinal side edge of the belt substrate layer and can form an elastic ring when the front and back belt portions 84, 86 are joined together. No elasticity may be provided in a portion of the central panel 80 of the front and back belt portions 84, 86 which overlaps with the front and back waist panels 52, 54 of the main body 38. This can be achieved by providing no elastic material in the central panel or deactivating any elastic materials present in the central panel. However, an elastic material may be provided in the central panel 80 if it is necessary.

Figure 5:
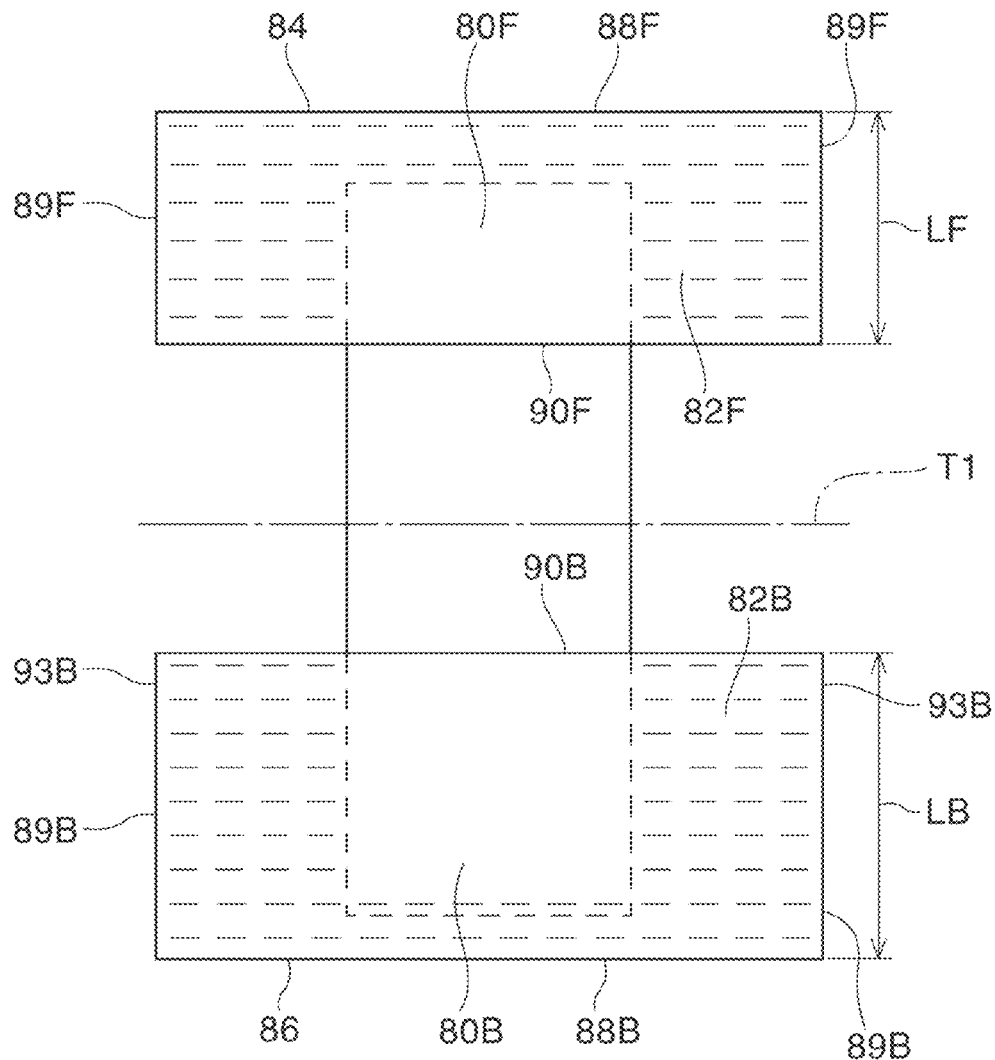
FIG. 5 is a schematic plan view of a preferred embodiment of the diaper of the present disclosure in its flat free-state condition showing the outer surface of the diaper.

As shown in FIG. 5, the front side panel 82F has a longitudinal length LF defined by the front side edge 89F of the front belt portion 84 and the back side panel 82B has a longitudinal length LB defined by the back side edge 89B of the back belt portion 86. In a preferred embodiment, the front belt portion 84 and the back belt portion 86 can be formed such that the longitudinal lengths LB of the back side panels 82B of the back belt portion 86 are greater than the longitudinal lengths LF of the front side panels 82F of the front belt portion 84. The front and back belt portions 84, 86 are formed by cutting a belt layer web along a cut line. The forming process will be described in detail hereinbelow. When the diaper is assembled to form the waist opening 36 and the leg openings 34, the diaper 20 is folded along the transverse centerline T1 such that the front distal edge 88F is aligned with the back distal edge 88B. The front side edge 89F is also aligned with a portion of the back side edge 89B. Then the front and back belt portions 84, 86 are joined at or adjacent to the front and back side edges 89F, 89B by the side seams 32. The front and back proximal edges 90F, 90B, however, are not aligned to one another. The back proximal edge 90B is disposed longitudinally closer than the front proximal edge 90F relative to the traverse centerline T1 such that the proximal portion 93B of the back side panel 82B extends toward the crotch panel 56 of the main body 38 beyond the front proximal edge 90F. The side edge of the proximal portion 93B is not joined to anywhere and is free from attachment. The ratio of the longitudinal length LB of the back side edge 89B to the longitudinal length LF of the front side edge 89F is optionally between about 1.1 and about 2.0, more optionally between about 1.2 and about 1.5 in a laid out flat configuration of the diaper. The diaper having these dimension characteristics provides an effective buttock cover without hindering the wearer from inserting legs into the leg opening.

Dimension of the Small-Sized Disposable Pull-on Diaper

The small-sized disposable pull-on diaper of the present disclosure has an optimized dimension and provides desirable ease of application and waist and leg fit properties.

Figure 6:
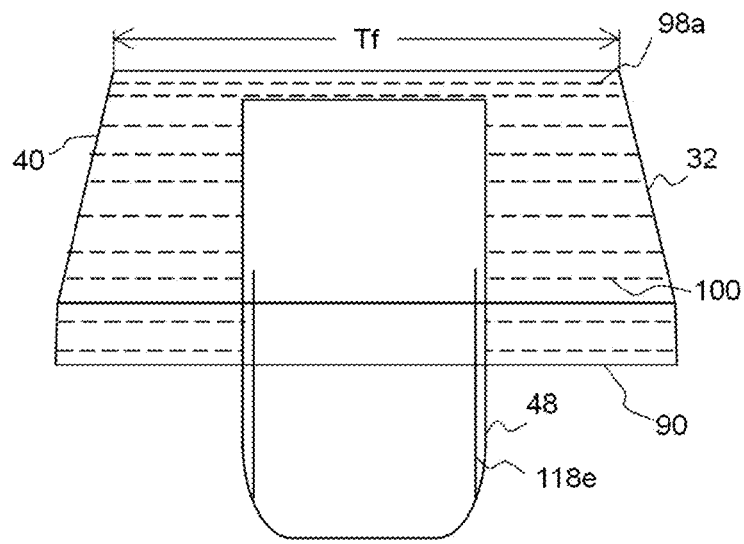
FIG. 6(a) is a schematic front view of a disposable pull-on diaper in a free-state.
FIG. 6(b) is a schematic front view of a disposable pull-on diaper in a stretched state.
FIG. 6(c) is a schematic right side view showing one of the leg openings of the diaper in shadow.
Figure 6:
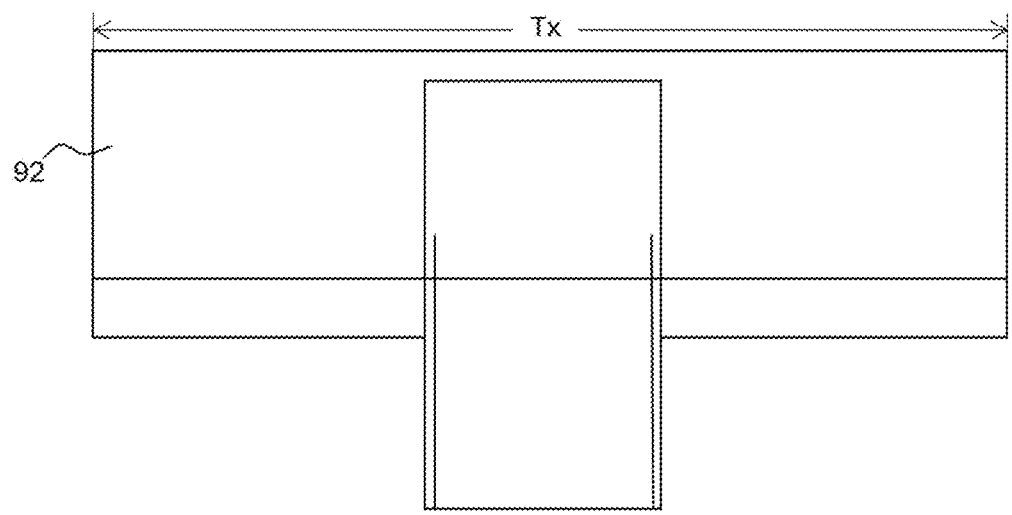
Figure 6:
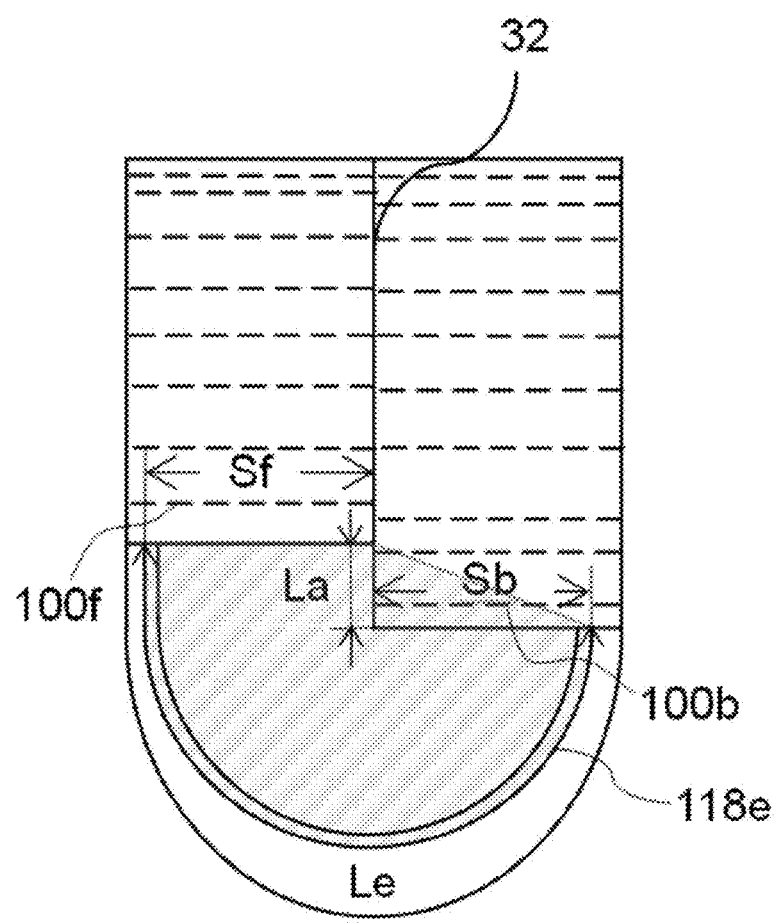

FIG. 6(a) is a schematic front view of a small-sized disposable pull-on diaper of the present disclosure in free state. FIG. 6(b) is a schematic front view of a small-sized disposable pull-on diaper of the present disclosure in stretched state. FIG. 6(c) is a schematic right side view of the small-sized disposable pull-on diaper in free state showing one of the leg openings in shadow. As used herein, "free state" refers to a state that the elastic material in the diaper is allowed to contract under an unused condition, and the diaper is free from any stretching force. As used herein, "stretched state" refers to a state that the ring-like elastic belt of the diaper is stretched to its maximum dimension which is substantially same to the dimension of the belt substrate layer with elastic strands being removed.

As shown in FIGS. 6(a) and 6(b), the diaper has a free-state waist circumferential length which is 2Tf, and a stretched waist circumferential length which is 2Tx. Tf indicates the dimension of the first waist elastic strand 98a from the distal edge 88 of the belt substrate layer 92 between the inner edge of the left and right side seams 32. The side seam may have a certain width, as shown in FIG. 1. For purposes of obtaining the free-state waist circumferential length and the stretched waist circumferential length, the inner, wearer facing side of the diaper is measured, excluding the width of the side seam. Tf is measured by carefully attaching a flexible tape measure ribbon along the first waist elastic strand 98a about every 10 mm to make sure that the tape measure ribbon follows the elastic strand, and then read the length in mm. Tx is the length of the same position as for measuring Tf where the ring-like elastic belt is stretched to its maximum length. Tx is substantially same to the length of the belt substrate layer 92 with the waist elastic strands 98 and side panel elastic strands 100 being removed away from the elastic belt. Tx can be measured by tearing a diaper down, such as by using a cold spray to facilitate the deactivation of adhesives attaching the elastic strands to the belt substrate layer. After the plurality of elastic strands 96 being removed and the substrate layer 92 being flattened, the length Tx is measured by a metal scale in mm.

As shown in FIG. 6(c), Sf indicates front side panel elastic length. Particularly, Sf is the length of the first side panel elastic strand 100f from the proximal edge 90F of the front side panel 82F in free state between the inner edge of the right side seam 32 and the cross point of the side panel elastic strand 100f and the first leg elastic strand material 118e from the side edge 48. Sb indicates back side panel elastic length. Particularly, Sb is the length of the first side panel elastic strand 100b from the proximal edge 90B of the back side panel 82B in free state between the inner edge of the right side seam 32 and the cross point of the side panel elastic strand 100b and the first leg elastic strand 118e from the side edge 48. Le indicates leg elastic length. Particularly, Le is the length of the leg elastic strand 118e closest to the side edge 48 in free state between the cross point of 118e with the front proximal edge 90F in front side panel 82F and the cross point of 118e with the back proximal edge 90B in back side panel 82B. Le can be measured by using the same method as described above with respect to the measurement of Tf. La indicates the difference in the longitudinal length of the front belt portion LF and back belt portion LB. Leg opening length can be calculated by the following formula:

$$\text{Leg opening length} = Le + Sf + \sqrt{Sb^2 + La^2}$$

where the front belt portion and back belt portion have the same longitudinal length, La will be zero, then the calculation of Leg opening length can be simplified as:

$$\text{Leg opening length} = Le + Sf + Sb.$$

The small-sized disposable pull-on diapers of the present disclosure has a stretched waist circumferential length from about 620 mm to about 700 mm, optionally from about 640 mm to about 680 mm, and the ratio of the stretched waist circumferential length to the free-state waist circumferential length is from about 2.5 to about 2.8, optionally from about 2.6 to about 2.7. In addition, the small-sized disposable pull-on diapers of the present disclosure has a leg opening length from about 250 mm to about 300 mm, optionally from about 265 mm to about 285 mm. Inventors of the present disclosure have found that small-sized pull-on diapers having the aforementioned dimensions provide the desirable ease of application as well as waist and leg fit. Without intending to be bound by theory, it is believed that the dimension of stretched waist circumferential length and the ratio of stretched waist circumferential length to free-state waist circumferential length as defined in the present disclosure provides a stretched waist opening which is wide enough to allow a caretaker to pull the diaper through an infant's legs with ease, meanwhile, the waist opening in free-state of the diaper will not be too big to cause sagging in use. Similarly, the dimension of leg opening length as defined in the present disclosure provides the desirable leg fit to a wearer. Leg opening length out of the range of the present disclosure may increase the incidence of leakage and gather mark.

In a preferred embodiment, leg elastic length Le presents from about 50% to about 75%, optionally, from about 68% to about 72% of the leg opening length. It has been found that the preferred percentage of leg elastic length Le in leg opening length provides a reduced incidence of leakage.

Figure 7:
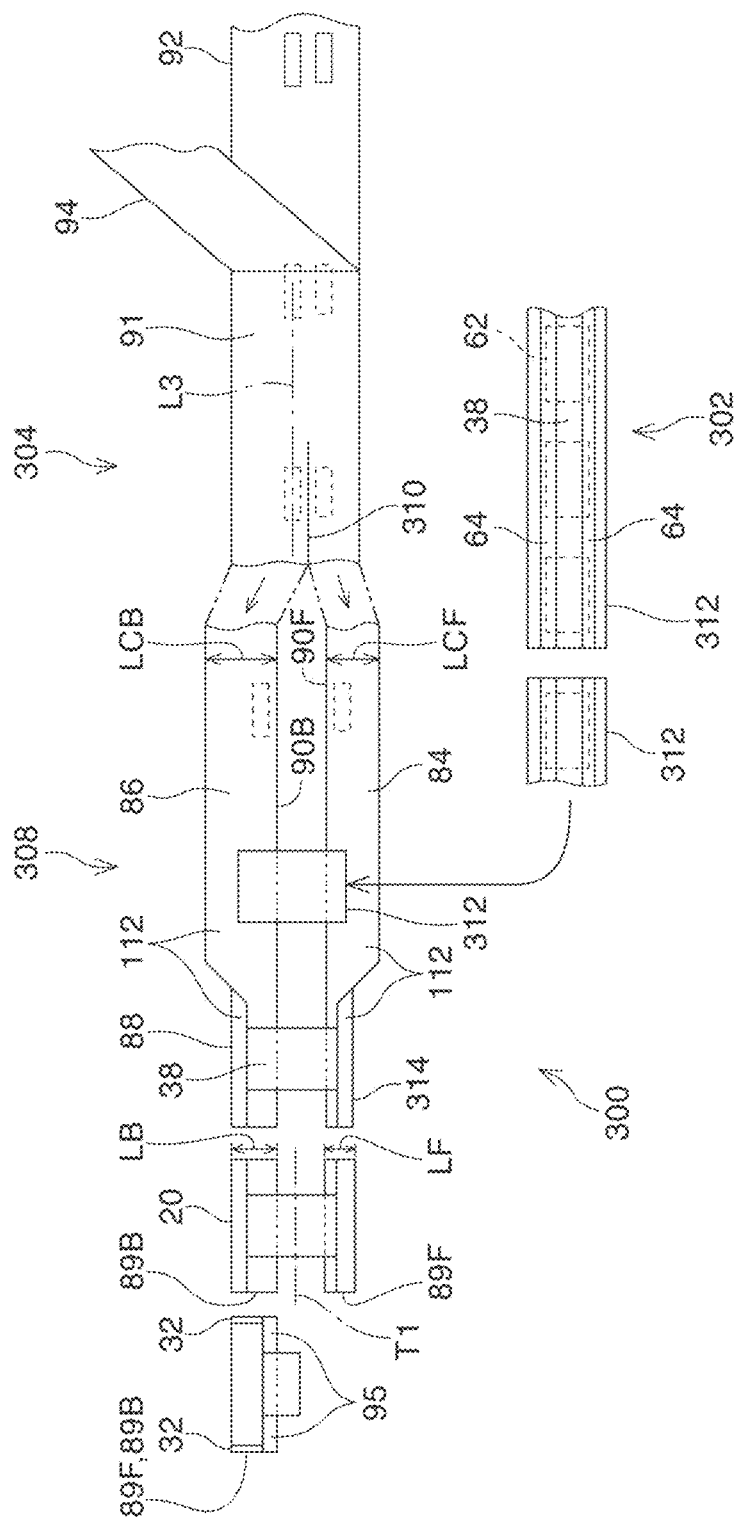
FIG. 7 is a schematic view showing the process for forming the pull-on diaper shown in FIG. 1.

FIG. 7 is a schematic view to explain the process for forming the diaper 20. The front and back belt portions 84, 86 are formed by cutting the belt layer web along a cut line 310. The process 300 shown in FIG. 7 primarily comprises three sections; a main body forming section 302, a belt forming section 304 and an assembly section 308. Since FIG. 7 is a schematic view, it should be noted that various parts of the diaper have been omitted, such as the belt and leg elastic material.

The main body forming section 302 combines elements forming the main body 38 such as the topsheet 58, the backsheet 60, the absorbent core 62 and the barrier leg cuff 64. The absorbent core 62 is sandwiched between the topsheet 58 and the absorbent core 62. The outer cover layer 42 (not shown in FIG. 7) is joined to the backsheet 60 (not shown in FIG. 7) and the leg elastic material 118 (not shown in FIG. 7) is sandwiched between the backsheet 60 and the outer cover layer 42. These elements are joined to each other by any known means such as adhesives or heat bonding to form an intermediate assembly 312. The intermediate assembly 312 is then cut into the individual intermediate assembly 312. The individual intermediate assembly 312 is turned by 90 degrees and fed into the assembly section 308.

The belt forming section 304 combines the belt substrate layer web 92 and the inner layer web 94 to form a continuous belt layer web 91. The continuous belt layer web 91 is cut along a straight cut line 310 which corresponds to the proximal edges 90F, 90B to form a continuous front belt web 84 and a continuous back belt web 86. The cut line 310 can be biased from the longitudinal centerline L3 of the continuous belt layer web 91 to differentiate the length LCF of the continuous front belt web 84 and the length LCB of the continuous back belt web 86 in the cross machine direction. The cross machine direction means the direction crossing the machine direction at a right angle. The machine direction means the direction where the component material is conveyed in the manufacturing process, which is in parallel to the longitudinal centerline L3. The belt elastic material 96 (not shown in FIG. 7) is also attached between the inner layer web 94 and the belt substrate layer web 92. Then the continuous front belt web 84 and the continuous back belt web 86 are separated from one another along the cur line 310.

The assembly section 308 combines the individual intermediate assembly 312 with the continuous front belt web 84 and the continuous back belt web 86. The individual intermediate assembly 312 is placed on the continuous front and back belt webs 84, 86 at a predetermined interval which become the side panel between each of the individual intermediate assemblies 312. The end flap 112 of the front and back belt webs 84, 86 is folded inwardly along the distal edge 88 to form a continuous diaper assembly 314 comprising the main body 38, the outer cover layer 42 (not shown in FIG. 7) and the front and back belt webs 84, 86. The continuous diaper assembly 314 thus formed is cut into each individual diaper 20. The individual diaper 20 has the longitudinal length LB of the back side edge 89B being greater than the longitudinal length LF of the front side edge 89F. The individual diaper 20 is then folded along the transverse centerline T1 in the crotch region and the front and back belt 84, 86 is joined at the side seams 32 adjacent to the side edges 89F, 89B to form the waist opening and the leg openings. Alternative methods for making the small-sized diapers of the present disclosure can be formed by a known process in the art, such as the process described in WO 2006/017718, the full disclosure of which is incorporated here by reference.

Examples

A small sized disposable pull-on diaper of the present disclosure is made according to a method described above and named as Example. Small-sized disposable pull-on diapers having similar structure to that of the present disclosure except dimensions as specified below are named as Comparative Example 1 and Comparative Example 2. Dimensions of the diapers of Example and Comparative Example 1 and 2 are shown in the following Table 1:

TABLE 1

|  | Example | Comparative Ex 1 | Comparative Ex 2 |
| --- | --- | --- | --- |
| Stretched waist circumferential length (2Tx) (mm) | 668.5 | 603.2 | 574.4 |
| Free-state waist circumferential length (2Tf) (mm) | 249.5 | 249.6 | 281.6 |
| Ratio of Tx/Tf | 2.68 | 2.42 | 2.04 |
| Leg opening length | 276.2 | 291.2 | 267.3 |

TABLE 1-continued

|  | Example | Comparative Ex 1 | Comparative Ex 2 |
| --- | --- | --- | --- |
| (mm) |  |  |  |
| Percentage of leg elastic length (Le) in Leg opening length | 69% | 77% | 60% |

The performance with respect to ease of application and waist and leg fit of the diapers of the above Example 1 and Comparative Example 1 and Comparative Example 2 are assessed as described below.

Ease of Application 6 panelists are asked to apply the test diapers to a standard small-sized baby mannequin in turn. Each panelist is asked to apply each of the diaper samples to the baby mannequin in turn and then rate the performance of ease of application of each tested sample in 5 scales from Very Poor to Excellent, wherein 5 represents Excellent, 4 represents Good, 3 represent Fair, 2 represent Poor and 1 represents Very Poor. The mannequin is a standard S-size full mannequin with legs in a curved position. The waist circumference and thigh circumference of the mannequin is 407 mm and 235 mm, respectively. The test result is shown in the following Table 2:

TABLE 2

| Ease of Application Test Result | | | |
| --- | --- | --- | --- |
| Panelist No. | Example a | Comparative Ex 1 b | Comparative Ex 2 c |
| 1 | 5 | 3 | 2 |
| 2 | 5 | 4 | 3 |
| 3 | 5 | 4 | 3 |
| 4 | 5 | 3 | 4 |
| 5 | 5 | 4 | 3 |
| 6 | 5 | 5 | 3 |
| Average | 5.0bc* | 3.8 | 3.0 |

*Statistically significant over Comparative Examples 1 and 2 with 90% confidence level Overall Fit Assessment Panelists who have babies having body weight of 4-8 kg are asked to use each test product for 5 days in turn. Panelists are asked to record the leakage, gather mark and sagging incidence observed when changing diapers each time. The incidence percentage is summarized in the following Table 3:

TABLE 3

|  | Example a | Comparative Ex 1 b |
| --- | --- | --- |
| Number of diapers used in total | 280 | 280 |
| Urine leakage % | 0b* | 2.1 |
| Gather mark % | 4b* | 10 |
| Sagging % | 27b* | 39 |

*Statistically significant over Comparative Example 1 with 90% confidence level

The Example diaper of the present disclosure has significant better performance in ease of application. While it may be intuitively expected that a diaper having ease of application may also have higher leakage and sagging occurrence, the Example diaper surprisingly provides significantly better urine leakage prevention and sagging prevention as well as reduced incidence of gather mark. It is believed that the defined dimensions of the present disclosure provide such unexpected benefit of improvement in ease of application, leakage prevention, gather mark and sagging prevention, at the same time.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable pull-on diaper comprising:
   a longitudinal axis and a lateral axis;
   an absorbent main body comprising a liquid pervious topsheet, a liquid impervious backsheet, and an absorbent core disposed therebetween;
   wherein the absorbent main body has left and right longitudinally extending side edges, and front and back transversely extending end edges that intersect with the longitudinally extending side edges at substantially a right angle, longitudinally opposing front and back waist panels, and a crotch panel between the waist panels, at least one leg elastic material disposed in proximity to each of said side edges and extending generally linearly and longitudinally, parallel with the longitudinal axis, along said side edges;
   a ring-like elastic belt comprising a front belt portion and a back belt portion joined to each other at side seams such that the back belt extends beyond the front belt at two leg openings, each of said front belt portion and back belt portion has transversely extending proximal and distal edges, the distal edge of the ring-like elastic belt defines a waist opening, the proximal edge being located closer than the distal edge relative to the crotch panel of the absorbent main body, each of said front belt portion and back belt portion has a central panel, and left and right side panels contiguous with its central panel;
   wherein the transversely extending proximal edges of the front and back belt portions are longitudinally offset from each other, but are parallel with each other and with the transverse axis;
   wherein the ring-like elastic belt comprises a belt substrate layer and a plurality of waist elastic strands and a plurality of side panel elastic strands each extending in the transverse direction, parallel with the lateral axis, and attached to the belt substrate layer;
   wherein said waist elastic strands are disposed in proximity to the distal edge and said side panel elastic strands are disposed at least in the left and right side panels, and wherein the ring-like elastic belt has a stretched waist circumferential length and a free-state waist circumferential length;
   wherein, the central panel of the front belt portion is joined to the front waist panel of the absorbent main body, the central panel of the back belt portion is joined to the back waist panel of the absorbent main body, and the proximal edge of the respective left and right side panels of the front belt portion and the back belt portion together with the left and right side edges of the crotch panel of the absorbent main body defines the two leg openings, each of the leg opening has a leg opening length which can be calculated according to the following formula:

$$\text{leg opening length} = Le + Sf + \sqrt{Sb^2 + La^2}$$

wherein Le indicates leg elastic length, Sf indicates front side panel elastic length, Sb indicates back side panel elastic length and La indicates the difference in a longitudinal length of the front belt portion and back belt portion; and
   wherein said stretched waist circumferential length is no greater than about 700 mm, and the ratio of the stretched waist circumferential length to the free-state waist circumferential length is from about 2.5 to about 2.8; and wherein said leg opening length is from about 250 mm to about 300 mm;
   wherein a longitudinal length of the front belt (LF) is less than a longitudinal length of the back belt (LB).

2. The diaper of claim 1, wherein said leg elastic length is from about 50% to 75% of the leg opening length.

3. The diaper of claim 1, wherein the stretched waist circumferential length is from about 640 mm to about 680 mm and the leg opening length is from about 270 mm to about 280 mm.

4. The diaper of claim 1, wherein the longitudinal length of the side panels of the back belt portion is greater than the longitudinal length of the respective side panels of the front belt portion.

5. The diaper of claim 4, wherein the ratio of the longitudinal length of each of the side panels of the back belt portion to the longitudinal length of the side panel of the front belt portion is between about 1.1 and about 2.0.

6. The diaper of claim 1, wherein the proximal edge and the distal edge of the ring-like elastic belt are substantially parallel.

7. The diaper of claim 1, wherein the plurality of side panel elastic strands are disposed only in the left and right side panels of the front and back belt portion.

8. The diaper of claim 1, wherein said waist elastic strands and side panel elastic strands are disposed at a different interval in the longitudinal direction.

9. The diaper of claim 1, further comprising an apertured film attached to the belt substrate layer.

10. A disposable pull-on diaper comprising:
    a longitudinal axis and a lateral axis;
    an absorbent main body comprising a liquid pervious topsheet, a liquid impervious backsheet, and an absorbent core disposed therebetween;
    wherein the absorbent main body has left and right side edges, and front and back end edges, longitudinally opposing front and back waist panels, and a crotch panel between the waist panels;
    a ring-like elastic belt comprising a front belt portion and a back belt portion joined to each other at side seams such that the back belt extends beyond the front belt at two leg openings;

wherein the ring-like elastic belt comprises a belt substrate layer and an apertured film attached to the belt substrate layer;

wherein, the central panel of the front belt portion is joined to the front waist panel of the absorbent main body, the central panel of the back belt portion is joined to the back waist panel of the absorbent main body, and a proximal edge of the respective left and right side panels of the front belt portion and the back belt portion together with the left and right side edges of the crotch panel of the absorbent main body defines the two leg openings, each of the leg opening has a leg opening length which can be calculated according to the following formula:

$$\text{leg opening length} = Le + Sf + \sqrt{Sb^2 + La^2}$$

wherein Le indicates leg elastic length, Sf indicates front side panel elastic length, Sb indicates back side panel elastic length and La indicates the difference in a longitudinal length of the front belt portion and back belt portion; and wherein a stretched waist circumferential length is no greater than about 700 mm, and the ratio of the stretched waist circumferential length to the free-state waist circumferential length is from about 2.5 to about 2.8; and wherein the leg opening length is no greater than about 300 mm;

wherein a longitudinal length of the front belt (LF) is less than a longitudinal length of the back belt (LB).

11. The diaper of claim 10, wherein the leg elastic length is from about 50% to 75% of the leg opening length.

12. The diaper of claim 10, wherein the stretched waist circumferential length is from about 640 mm to about 680 mm and the leg opening length is from about 270 mm to about 280 mm.

13. The diaper of claim 10, wherein the longitudinal length of the side panels of the back belt portion is greater than the longitudinal length of the respective side panels of the front belt portion.

14. The diaper of claim 13, wherein the ratio of the longitudinal length of each of the side panels of the back belt portion to the longitudinal length of the side panel of the front belt portion is between about 1.1 and about 2.0.

15. The diaper of claim 10, wherein the proximal edge and the distal edge of the ring-like elastic belt are substantially parallel.

16. The diaper of claim 10, wherein a plurality of side panel elastic strands are disposed only in the left and right side panels of the front and back belt portion.

17. The diaper of claim 10, further comprising a plurality of elastic strands attached to the belt substrate layer.

18. The diaper of claim 17, wherein the plurality of waist elastic strands are disposed at different intervals in the longitudinal direction.

19. The diaper of claim 10, wherein the absorbent core comprises cellulose.

20. The diaper of claim 10, further comprising a cuff having a folded proximal edge, wherein the proximal edge of the cuff overlaps the absorbent core.

* * * * *